US012740937B2

(12) United States Patent
Santino Turnbull

(10) Patent No.: US 12,740,937 B2
(45) Date of Patent: Sep. 22, 2026

(54) OINTMENT OR BALM AND METHOD FOR PRODUCING SAME

(71) Applicant: Alicia Marie Santino Turnbull, Grosse Pointe Park, MI (US)

(72) Inventor: Alicia Marie Santino Turnbull, Grosse Pointe Park, MI (US)

( * ) Notice: Subject to any disclaimer, the term of this patent is extended or adjusted under 35 U.S.C. 154(b) by 237 days.

(21) Appl. No.: 18/538,531

(22) Filed: Dec. 13, 2023

(65) Prior Publication Data

US 2024/0197619 A1 Jun. 20, 2024

Related U.S. Application Data

(60) Provisional application No. 63/432,588, filed on Dec. 14, 2022.

(51) Int. Cl.

| | |
|---|---|
| ***A61K 8/92*** | (2006.01) |
| ***A61K 8/9789*** | (2017.01) |
| ***A61K 8/9794*** | (2017.01) |
| ***A61Q 19/00*** | (2006.01) |

(52) U.S. Cl.

CPC ............ *A61K 8/9789* (2017.08); *A61K 8/922* (2013.01); *A61K 8/927* (2013.01); *A61K 8/9794* (2017.08); *A61Q 19/001* (2013.01)

(58) Field of Classification Search

CPC ...... A61K 8/9789; A61K 8/922; A61K 8/927; A61K 8/9794; A61Q 19/001

See application file for complete search history.

(56) References Cited

U.S. PATENT DOCUMENTS

| | | | | |
|---|---|---|---|---|
| 5,830,915 | A | 11/1998 | Pikul et al. | |
| 8,512,718 | B2 | 8/2013 | Eini et al. | |
| 9,700,507 | B1 | 7/2017 | Hakim | |
| 9,732,071 | B2 | 8/2017 | Patron et al. | |
| 11,985,994 | B2 * | 5/2024 | Shi | C13K 13/002 |
| 2014/0287064 | A1 * | 9/2014 | Swenholt | A61K 31/045 424/665 |
| 2014/0349943 | A1 * | 11/2014 | Gadek | A61K 9/08 514/18.7 |
| 2016/0095890 | A1 | 4/2016 | Stancioiu et al. | |
| 2016/0135489 | A1 | 5/2016 | Batenburg et al. | |
| 2016/0310526 | A1 * | 10/2016 | Swenholt | A61K 33/20 |
| 2022/0332777 | A1 * | 10/2022 | Cooper | A61P 31/04 |

FOREIGN PATENT DOCUMENTS

| | | | |
|---|---|---|---|
| EP | 3356356 | B1 | 5/2021 |
| WO | 2022147470 | A1 | 7/2022 |

OTHER PUBLICATIONS

Villiers, Ointment Bases. LWBK127-C23[277-290].qxd Oct. 19, 2008 (Year: 2008).*

* cited by examiner

*Primary Examiner* — Robert A Wax
*Assistant Examiner* — Ngoc-Anh Thi Nguyen
(74) *Attorney, Agent, or Firm* — Howard & Howard Attorneys PLLC

(57) ABSTRACT

An ointment or a balm for use topical application to the skin, lips or mouth of a human includes an infused mixture that is mixed with melted beeswax and cooled to harden the beeswax. The infused mixture includes an oil mixture infused with a dried and coated shredded potato. The dried and coated shredded potato is formed by soaking and subsequently drying a shredded potato with a combination of baking soda and vinegar.

18 Claims, 1 Drawing Sheet

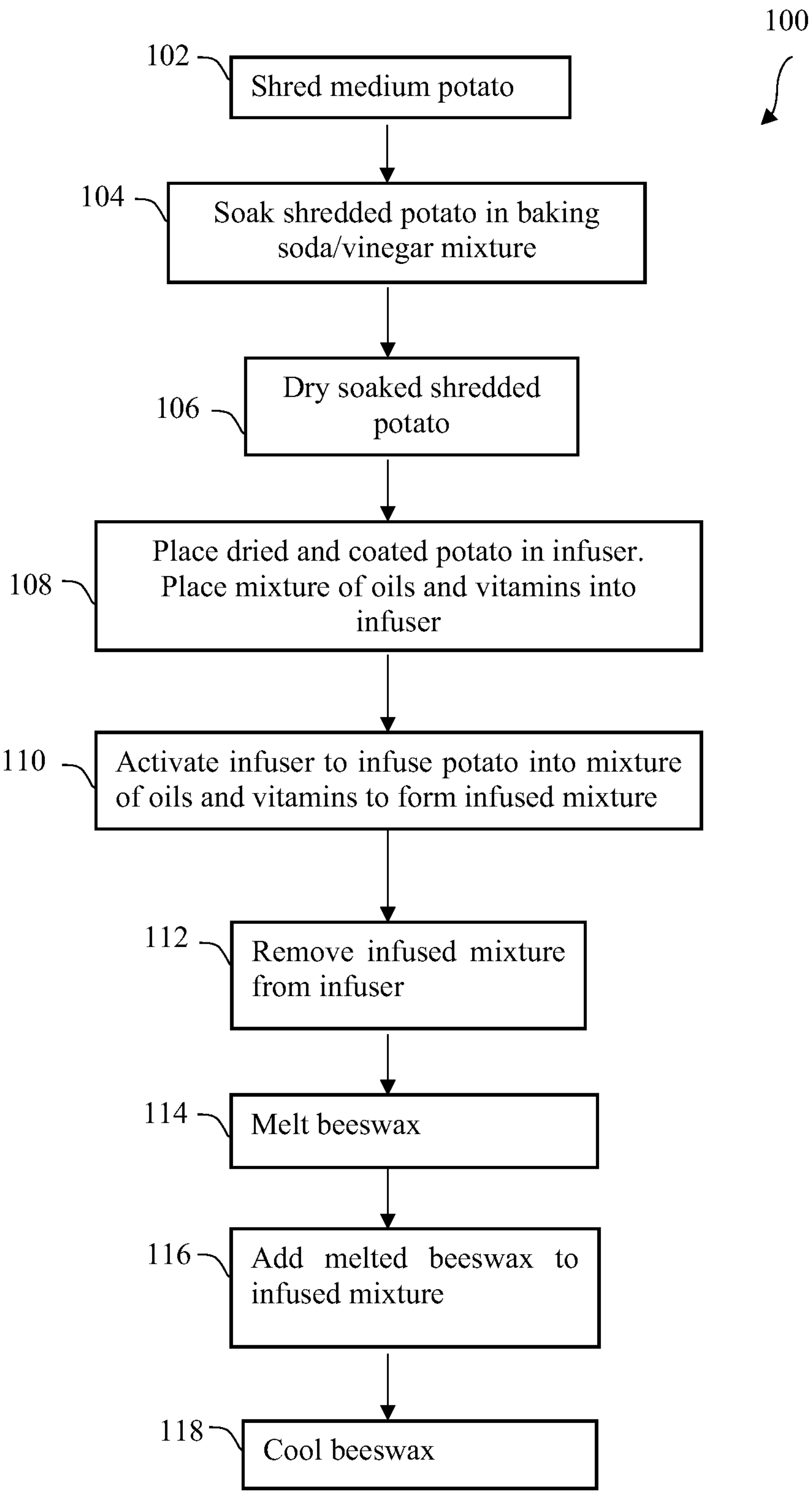
100
102
Shred medium potato
104
Soak shredded potato in baking soda/vinegar mixture
106
Dry soaked shredded potato
108
Place dried and coated potato in infuser. Place mixture of oils and vitamins into infuser
110
Activate infuser to infuse potato into mixture of oils and vitamins to form infused mixture
112
Remove infused mixture from infuser
114
Melt beeswax
116
Add melted beeswax to infused mixture
118
Cool beeswax

OINTMENT OR BALM AND METHOD FOR PRODUCING SAME

CROSS-REFERENCE TO RELATED APPLICATIONS

The present application claims priority to and all the benefits of U.S. Provisional Patent Application No. 63/432,588, filed on Dec. 14, 2022, and entitled "Ointment/Balm", the entire contents of which are expressly incorporated herein by reference.

FIELD OF THE DISCLOSURE

The present disclosure relates to ointments or balms for topical application to the skin, lips and mouth of a human.

SUMMARY OF THE DISCLOSURE

The present disclosure relates to a method for forming an ointment or a balm and associated ointments or balms formed in accordance with this method. The method includes the step of forming a soaked potato by soaking a shredded potato in a mixture of baking soda and vinegar. The method also includes the steps of forming a dried and coated potato by drying the soaked potato to remove residual moisture; introducing the dried and coated potato to an infusing machine; placing an oil mixture into the infusing machine; forming an infused product by actuating the infusing machine to infuse the dried and coated potato with the oil mixture; melting a quantity of beeswax; combining the infused product with the quantity of melted beeswax; and cooling the beeswax below its melting temperature to form the ointment or the balm. In these ointments or balms formed by the method, the volume of beeswax relative to the volume of the oil mixture varies from 0.5 to 2 fluid ounces of beeswax relative to 12 to 13 fluid ounces of the oil mixture in the ointment or balm.

The subject disclosure also contemplates the topical application of the ointment or balm, as formed in accordance with the subject disclosure, to the skin, lips or within the mouth of a human.

BRIEF DESCRIPTION OF THE DRAWINGS

Other advantages of the subject disclosure will be readily appreciated, as the same becomes better understood by reference to the following detailed description when considered in connection with the accompanying drawings.

FIG. 1 is a logic flow diagram for forming an ointment or balm in accordance with the subject disclosure.

DETAILED DESCRIPTION OF THE DISCLOSURE

The subject disclosure is directed to an ointment, or balm, for topical application to the skin, lips and mouth of a human, as well as an associated method for making the ointment or balm and the subsequent use of the ointment or balm on a human.

The topical application of the ointment or balm to the skin, lips or within the mouth of a human may relieve, renew, rejuvenate, regenerate and restore skin burns, sun burns, cuts, wounds, skin damage, anti-inflammatory, and insect bites. In addition, topical application of the ointment or balm to the skin may clears complexion, brighten skin, remove or minimize dark spots diminish stretch marks, and minimize acne. In addition, the topical application of the ointment or balm to the skin may assist in skin balancing, skin tightening, skin toning and the like while also moisturizing the skin.

As used herein, the term "ounces" may refer to a weight measure or to a volume measure corresponding to a liquid. In other words, liquids provided herein may be referred to as having a volume in "fluid ounces", whereas other materials or ingredients may be measured as a weight in ounces, which refers to 1/16 of a pound.

The ointment or balm, in general, is formed by infusing a plurality of different types of oils and vitamins (i.e., vitamin oils) of select compositions with a shredded potato, presoaked and subsequently dried in a mixture of baking soda and vinegar, and then mixing the infused potato with melted beeswax and allowing the beeswax to harden to form the ointment or balm.

The potato utilized can be of the more than two-hundred variety of potatoes sold throughout the United States and around the world. Each of these varieties fit into one of seven generally accepted potato type categories, including russet, red, white, yellow, blue/purple, fingerling, and petite. One-half of a medium-sized or large-sized russet, white or yellow potatoes are preferably utilized.

A medium-sized potato, as defined herein, is a potato that is generally 2.25 to 3.25 inches in diameter (i.e., 5.7 to 7.7 centimeters in diameter) and weighs between 0.3125 and 0.625 pounds (i.e., 5-10 ounces or 140-280 grams). Potatoes of slightly larger size (i.e., large potatoes) may also be utilized, while adjusting the remainder of the components used to make the ointment or balm in conjunction therewith. A large-sized potato, as defined herein, is a potato that is larger than the medium-sized potato as described above and generally weighs between 0.625 and 0.75 pounds (i.e., between 10 and 12 ounces or between 280 and 340 grams).

Preferably, the potato utilized is an organic potato. Organic potatoes, as defined herein, are potatoes that are grown using organic farming methods. Organic farmers use natural alternatives, such as compost, manure, and crop rotation, to enhance soil fertility and control pests. Organic farming relies on natural fertilizers. Synthetic fertilizers are avoided. Organic standards prohibit the use of genetically modified organisms (GMOs).

Organic potatoes are less likely to have synthetic pesticide residues, as they are grown without the use of such chemicals. Organic farming practices emphasize soil health through methods such as crop rotation and the use of cover crops, contributing to sustainable agriculture.

The mixture used to soak the medium-sized or large-sized and shredded potato is preferably a 50/50 percentage by weight of baking soda and vinegar. Of course, in other embodiments, the weight percentages of the baking soda and vinegar may vary, such as from 10/90 weight percentage to a 90/10 weight percentage. The relative amount/volume of baking soda and vinegar is included preferably is sufficient or otherwise adequate to cover the outer surface of the shredded potato.

In certain embodiments, about one-third (i.e., 1/3) or one-half (i.e., 1/2) of a cup (i.e., a standard measuring cup used in the United States for measuring liquids or solids) of baking soda is added to one-half of a shredded medium-sized potato or a shredded large-sized potato for forming the ointment or balm. Relatedly, in certain embodiments, about one-third (i.e., 1/3) or one-half (i.e., 1/2) of a cup (i.e., a standard measuring cup—corresponding to four fluid ounces) of vinegar is added to one-half of a shredded medium-sized potato or a shredded large-sized potato for forming the ointment or balm. The relative amounts of baking soda and vinegar may vary from the ⅓rd to ½ cup for covering the half of the shredded medium-sized or large-sized potato, with the amount being sufficient to fully cover the surface of the shredded potato in the soaking step, as described below, in order to cover the shredded potato to form the dried and coated potato that is subsequently infused, as described below.

Thes mixture is soaked with the shredded potato for a sufficient time to break down fibers of the shredded potatoes to form a soaked potato, such as for approximately 15 to 30 minutes or more. Preferably, the soaking of the shredded potato is done at room temperature, although the temperature may be elevated above room temperature.

Preferably, the baking soda is organic baking soda or pure baking soda, although any type of baking soda may be utilized.

Manufacturers may produce organic baking soda using more environmentally friendly and sustainable practices. They might use more ecologically responsible methods in the extraction or mining of the raw materials. Organic baking soda is typically free from synthetic additives, aluminum, and other chemicals.

Pure baking soda typically suggests that the baking soda is free from additives, impurities, or contaminants. Pure baking soda indicates a high level of purity in terms of the sodium bicarbonate content. Pure baking soda should not contain additional chemicals, anti-caking agents, or fillers.

Still further, it is preferable that the vinegar is an organic vinegar. Still further, in certain embodiments, the vinegar utilized is suitable for culinary uses, particularly where the ointment or balm is applied to the lips or within the mouth of a human or animal and thus may be ingested. One exemplary vinegar for culinary use that may be utilized is apple cider vinegar. Other suitable vinegars suitable for culinary use that that could be used, alone or in combination (including in combination with apple cider vinegar), include distilled white vinegar (i.e., white vinegar), white wine vinegar, balsamic vinegar, champagne vinegar, red wine vinegar, sherry vinegar, rice vinegar, red rice vinegar, black vinegar, cane vinegar, beer vinegar, coconut vinegar, raisin vinegar, or malt vinegar.

In certain embodiments, the vinegar utilized in an organic apple cider vinegar (ACV). Organic ACV is made from apples that are grown using organic farming practices. This means that the apples are cultivated without the use of synthetic pesticides, herbicides, or genetically modified organisms (GMOs). Organic farming focuses on sustainable and environmentally friendly methods with such chemicals being prohibited. Organic ACV is typically made with a focus on natural and minimal processing. It may not contain synthetic additives or preservatives, and the fermentation process is often allowed to occur naturally. Organic ACV is produced in accordance with organic farming standards, and products labeled as organic must meet specific criteria set by certification bodies. In the context of apple cider vinegar (ACV), the term "mother" refers to a colony of beneficial bacteria and acetic acid-forming bacteria, along with strands of proteins, enzymes, and beneficial microorganisms that develop during the fermentation process. The vinegar is unpasteurized and contains live, beneficial components.

Once the potato is soaked for a sufficient time to break down fibers of the shredded potatoes to form a soaked potato, as noted above, the resultant soaked potato is dried for a sufficient period to remove residual moisture from the potato to form the dried and coated potato, in which the shredded potato is coated with the vinegar and baking soda mixture. Preferably, the drying occurs at room temperature or a slightly elevated temperature above room temperature sufficient to remove moisture, in the form of the liquid component of the vinegar and any residual water from the shredded potato, such that the shredded potato coated with the vinegar and baking soda mixture is moist to the touch but not dripping. The time sufficient to dry the potato may vary from a few minutes to a few hours.

Next, the dried and coated potato is infused with an oil mixture (i.e., a mixture of oils) and optionally with additional vitamins or components within an infusing machine (i.e., an infuser).

The infuser that can be utilized can be any commercially available infuser. One infuser that is suitable for use is LEVO brand infusers, commercially available from LEVO Oil Infusion, LLC of Denver Colorado. The LEVO brand infusers infuse the oil mixture at a temperature of 175-185 degrees Fahrenheit (about 79 to 85 degrees Celsius) for a total of 2.5 hours or more.

The oils that can be utilized in the oil mixture include almond oil, jojoba oil, aragon oil, cannabidiol ("cbd") oil, aloe vera, vitamin E oil, vitamin C oil, and other types of essential oils (i.e., concentrated plant extracts such as but not limited to lavender oil, tea tree oil, frankincense oil, peppermint oil, lemon oil, lemongrass oil, orange oil, rosemary oil, or bergamot oil) that are safe for ingestion or topical application in non-concentrated forms. Still further oils may include ginger oil, rosehip oil, neem oil, black seed oil, rosemary oil, neroli oil, carrot oil and carrot seed oil. In topical ointments or balms, other essential oils not suitable for ingestion can be used in minor amounts, including but not limited to arborvitae oil, birch oil, cedarwood oil, cypress oil, *eucalyptus* oil, white fir oil, or wintergreen oil.

In certain embodiments, oils added in larger amounts, such as jojoba oil or almond oil, are included as carrier oils for the essential oils described above, with the essential oils provided a desired therapeutic benefit to the skin, lips or mouth. In particular, the carrier oils are used to dilute the essential oils and are provided to limit or minimize any irritation when otherwise potent essential oils are applied topically to the skin, lips or within the mouth of a human. The carrier oils may function therefore to "carry" the essential oils to the skin surface, the lips surface, or the surface of the mouth to which the ointment or balm is applied.

As used herein, the term "tea tree oil" refers to distillates of the leaves of the Australian tree, *Melaleuca* alternifolia. Tea tree oil is assigned the Chemical Abstract number 68647-73-4 and is commercially available from a variety of sources.

Preferably, the oils described derived from plants or crops are organic oils. Organic oils are typically derived from crops that are non-genetically modified. Organic farming practices prioritize soil health using compost, crop rotation, and other sustainable methods. Organic oils are produced in accordance with organic farming standards, and products labeled as organic that meet specific criteria set by certification bodies.

In certain embodiments, and preferably, the oil mixture includes almond oil and vitamin E oil.

In certain embodiments, additional vitamins or components that may not be considered an oil may be included. One example is aloe vera, and in particular pure aloe vera, may be included. Pure aloe vera, as defined herein, is a product that contains a high concentration of aloe vera extract without significant additives, fillers, or synthetic ingredients.

Even still further, in certain embodiments, the total volume of the oil mixture (which may also include the afore-mentioned vitamins and/or other components such as aloe vera as described above) ranges from about 10-15 fluid ounces, such as 12.25 fluid ounces, per one half of a shredded medium-sized potato or a shredded large-sized potato (i.e., between 140 and 170 grams of shredded potato), as illustrated in the examples below. Stated another way, in certain embodiments, the total amount of the oil mixture (which may also include the afore-mentioned vitamins and/or other components such as aloe vera as described above) ranges from about 20-30 fluid ounces, such as 24.5 fluid ounces, per shredded medium-sized or large-sized potato.

The method 100 for forming the balm or ointment including the components described above is illustrated in a logic flow diagram of FIG. 1 described below.

The method 100 begins with step 102, in which the potato is shredded (medium-sized or large-sized) into thin strips prior to use utilizing any commonly available shredding apparatus, including but not limited to a hand grater, mandoline, julienne blade or an electric stand mixer with a prep slicer/shredder attachment. Optionally, the potato may be peeled prior to shredding. Alternatively, a medium-sized or large-sized potato is provided in shredded form in step 102.

Next, in step 104, the potato shredded in step 102 or otherwise provided in shredded form in step 102 is placed onto a dish or in a shallow container and the shredded potato is soaked in a mixture of the baking soda and vinegar (as described above) for a sufficient time to break down fibers of the shredded potatoes to form a soaked potato, such as for approximately 15 to 30 minutes or more. The amount of baking soda and vinegar may vary but should be sufficient in volume to cover the shredded potato for soaking. Preferably, the soaking of the shredded potato is done at room temperature, although the temperature may be elevated above room temperature.

Next, in step 106, the soaked potato is dried for a sufficient period to remove residual moisture from the potato to form the dried and coated potato (i.e., wherein the potato is coated with the vinegar and baking soda mixture). In certain embodiments, the drying process is done on the dish or in a shallow container of step 104, typically for a period of three hours or more but wherein the period may vary from a few minutes to a few hours. Alternatively, the shredded potato mixed with the baking soda and vinegar are introduced to an infusion machine (i.e., an infuser) and dried for three hours, although the length of the drying process may vary between a shorter time or longer time than three hours depending upon the type of infuser used and whether heat is introduced during the drying process.

As described herein, the term "dried" does not infer or otherwise imply that the potato is completely free from moisture. The term "dried", as noted above, means that residual moisture (i.e., droplets of moisture) is removed from the potato—the potato still includes moisture from the applied vinegar in liquid form and/or water content from the potato itself and may be moist to the touch while droplets of moisture are generally not present.

Next, in step 108, the dried and coated shredded potato is placed into the infuser (if not already performed as part of step 106). The oil mixture (described above) and vitamins are placed or otherwise introduced to the infuser, such as on a shelf beneath the dried and coated shredded or otherwise onto the shelf containing the potato and the infuser is closed. As noted above, the relative volume amount of the oil mixture added is dependent upon the relative weight amount of dried and coated potato placed into the infuser, as described above.

In step 110, the infuser is actuated, and the dried and coated potato is infused into the oil mixture and optionally vitamins and other components (collectively sometimes referred to simply as a mixture or oil mixture) to form an infused mixture. Preferably, the infusion process is completed in approximately two to five hours, depending upon the potency of the ointment or balm desired, with an increase in time resulting in increased potency of the infused product. In certain embodiments, the infusion takes place at room temperatures, while in other embodiments the temperature is raised to a temperature above room temperature, such as to a temperature between 175- and 200-degrees Fahrenheit (i.e., about 79 to 83 degrees Celsius).

In step 112, and upon completion of step 110, the oil mixture and vitamins and other components infused with the dried and coated potato (i.e., the infused mixture) is dripped out of the infuser, or otherwise removed from the infuser, and into a container. The dripped mixture is hereinafter referred to as the "infused product".

In step 114, beeswax is melted, such as by placing unmelted beeswax in a glass measuring cup or jar placed within a container of boiling water for a sufficient time to raise the temperature of the beeswax above its melting temperature (approximately 145 degrees Fahrenheit, or 63 degrees Celsius) to completely melt the beeswax.

The term "beeswax", as described herein, refers to the natural substance secreted by honeybees. There are three main types of beeswax, including yellow beeswax, white beeswax, and absolute beeswax. Yellow beeswax is the natural, unrefined, and raw wax derived directly from the honeycomb. Yellow beeswax may vary in color and can be yellow, brown, or orange to golden depending upon the types of flowers that the honeybee got nectar from, but all are considered in general to be "yellow beeswax" as defined herein. White beeswax is the result of yellow beeswax undergoing a filtering/purifying/bleaching process. Absolute beeswax is the result of treating yellow beeswax with alcohol. Preferably, yellow beeswax or white beeswax is utilized in the subject disclosure.

In certain embodiments, the yellow beeswax utilized is pure beeswax (i.e., pure yellow beeswax), in which the yellow beeswax has been filtered to remove impurities.

In step 116, the melted beeswax is placed into a container, such as a canning jar, and the infused product is added to the melted beeswax. The infused product and melted beeswax can be stirred to ensure an equal or otherwise substantially uniform distribution of the infused mixture within the melted beeswax. Preferably, the infused product is added at an elevated temperature to ensure complete and thorough mixing while the beeswax remains completely melted to ensure even distribution.

As a part of step 116, in certain embodiments, the mixture of the melted beeswax and infused product may be transferred into any number of smaller, individual containers or jars for subsequent use.

In step 118, the melted beeswax containing the infused mixture (which was placed in the container in step 116) is allowed to cool to reharden the melted beeswax, thereby forming the ointment or balm with the container or containers that includes the infused mixture generally uniformly distributed within the hardened beeswax, with the difference between whether the ointment and balm is formed being in the relative proportions of beeswax and the infused mixture present in the container. As the relative amount of beeswax relative to the amount of infused mixture is increased, the resultant mixture after cooling within the container forms a balm. At lower levels of beeswax, the resultant mixture forms an ointment. In other words, the ointment contains a smaller proportional amount (by weight or volume) of beeswax relative to the infused mixture than the balm.

In general, the volume of beeswax relative to the volume of the oil mixture in the ointment or balm may vary from 0.5 fluid ounces to 2 fluid ounces of beeswax (measured typically in a liquid form) per 12-13 ounces of the oil mixture depending upon the desired hardness of the ointment or balm desired, with the increase in hardness transitioning the formed product from an ointment to a balm as the hardness is increased. Stated another way, the volume ratio of beeswax to the oil mixture varies from between 0.5:13 (i.e., 1:26) to 2:12 (i.e., 1:6), with an increase in the relative proportion of the volume of beeswax to the oil mixture resulting in an increased hardness in the formed resultant product once the beeswax is cooled.

In ointments, in certain embodiments, approximately 1 to 1.25 fluid ounces of beeswax is included per 12-13 ounces of the oil mixture in the resultant product, while in balms the relative amount of beeswax is increased to greater than 1.5 fluid ounces to 2 ounces per 12-13 ounces of the oil mixture prior to infusion in the formed resultant product.

In an alternative method of forming the balm or ointment, the beeswax can be introduced within the infusion machine during the infusion process instead of being mixed with the infused product after its formation as described in steps 110-118 of FIG. 1 above. The beeswax will melt within the infusion machine while the machine is actuated, particularly where the temperature of the infuser is increased to above the melting temperature of the beeswax (approximately 145 degrees Fahrenheit or 63 degrees Celsius) and mix with the infused oils and vitamins in a manner like the process of FIG. 1 above.

The subject disclosure contemplates the use of the ointment, or the balm, formed in accordance with the method herein, for use on a human. The topical application of the ointment or balm to the skin, lips or within the mouth of a human may relieve, renew, rejuvenate, regenerate and restore skin burns, sun burns, cuts, wounds, and skin damage. The ointment or balm may provide benefits as an anti-inflammatory and can be applied to insect bites. In addition, topical application of the ointment or balm to the skin may clears complexion, brighten skin, remove or minimize dark spots diminish stretch marks, and minimize acne. In addition, the topical application of the ointment or balm to the skin may assist in skin balancing, skin tightening, skin toning and the like while also moisturizing the skin. Accordingly, the application of the ointment or balm to the skin may increase the youthful appearance of the skin. The varying combination of the oils described above, in various amounts, can be tailored to achieve a desired effect to the skin or lips or mouth as described above and are illustrated in a limited group of Examples below.

Further, and because certain embodiments of the subject disclosure of the ointment or balm contains no known harmful components that can be ingested by a human, the ointment or balm can also be applied to burns or other wounds on the lips or within the mouth, such as on the tongue.

EXAMPLES

In the Examples provided below, organic ingredients and pure ingredients are provided. However, such Examples are exemplary and non-limiting. Accordingly, in further related examples, non-organic ingredients commercially available ingredients that are not deemed "pure" by a particular standard may be substituted for any one or more ingredients listed below.

In one example, an ointment for burns, cuts, wounds, and insect bites is formed from the ingredients/components described in Table 1 below according to the following procedure:

TABLE 1

| Ingredient/Component | Weight or Volume |
|---|---|
| Organic Jojoba Oil | 10.25 fluid ounces |
| Organic Lavender Oil | 0.25 fluid ounces |
| Pure Aloe Vera | 0.25 fluid ounces |
| Organic Vitamin E Oil | 0.25 fluid ounces |
| Organic Rosehip Oil | 0.25 fluid ounces |
| Organic Neem Oil | 0.25 fluid ounces |
| Organic Ginger Oil | 0.25 fluid ounces |
| Organic Black Seed Oil | 0.25 fluid ounces |
| Organic Peppermint Oil | 0.25 fluid ounces |
| Large Organic Potato | ½, shredded (about 140 grams) |
| Organic or Pure Baking Soda | ½ cup (standard measuring cup) |
| Organic Apple Cider Vinegar | ½ cup (standard measuring cup - about 4 fluid ounces) |
| Pure Yellow Beeswax | 1.25 fluid ounces (ointment) or 1.5 fluid ounces (balm) |

First, the ½ of a large size potato is shredded and placed on a dish. The shredded potato is soaked in a mixture of the organic or pure baking soda and organic apple cider vinegar for 20 minutes. The shredded potato coated with the organic or pure baking soda and organic apple cider vinegar is allowed to dry at room temperature to form a dried and coated potato. The dried and coated potato may be moist to the touch.

The dried and coated potato is introduced to an infusion machine, here a LEVO brand infuser such as the LEVO 2 or LEVO Lux infuser. The mixture of the oils, totaling 12.5 fluid ounces as listed above is placed into the bottom of the infusion machine, and the infusion machine is actuated for approximately two to five hours. During this actuation, the dried and coated potato is infused into the mixture to form an infused mixture, with the longer infusion times resulting in an increased degree of infusion and hence potency of the infused mixture. The infusion machine is turned off, and the infused mixture is dripped into a jar or container.

Next, the beeswax is introduced to a container, such as a glass measuring cup, which is placed into a pot of boiling water for a sufficient period to melt the beeswax (i.e., to raise the temperature of the beeswax above its melting temperature of approximately 145 degrees Fahrenheit). The melted beeswax is then poured into a canning jar, and the infused mixture is added to the melted beeswax. The resultant mixture is allowed to cool, and the beeswax hardens. The combination of the infused mixture and the hardened beeswax forms an ointment that is suitable for application topically on the skin or lips of a human or within the mouth of a human.

To form a balm in accordance with this Example, the same procedure, but the relative amount of beeswax is increased to 1.25 to 1.5 fluid ounces while the remainder of the components relative amounts remains the same.

In yet another example, a clear skin ointment is formed from the ingredients/components described in Table 2 below according to the following procedure:

TABLE 2

| Ingredient/Component | Weight or Volume |
|---|---|
| Organic Jojoba Oil | 10.25 fluid ounces |
| Organic Rosehip Oil | 0.5 fluid ounces |
| Organic Lemon Oil | 0.5 fluid ounces |
| Organic Lavender Oil | 0.25 fluid ounces |
| Organic Tea Tree Oil | 0.5 fluid ounces |
| Organic Rosemary Oil | 0.25 fluid ounces |
| Organic Black Seed Oil | 0.25 fluid ounces |
| Large Organic Potato | ½, shredded (about 140 grams) |
| Organic or Pure Baking Soda | ½ cup (standard measuring cup) |
| Organic Apple Cider Vinegar | ½ cup (standard measuring cup - about 4 fluid ounces) |
| Pure Beeswax | 1.25 fluid ounces (ointment) or 1.5 fluid ounces (balm) |

First, the ½ of a large size potato is shredded and placed on a dish. The shredded potato is soaked in a mixture of the organic or pure baking soda and organic apple cider vinegar for 20 minutes. The shredded potato coated with the organic or pure baking soda and organic apple cider vinegar is allowed to dry at room temperature to form a dried and coated potato. The dried and coated potato may be moist to the touch.

The dried and coated potato is introduced to an infusion machine, here a LEVO brand infuser such as the LEVO 2 or LEVO Lux infuser. The mixture of the oils, totaling 12.5 fluid ounces as listed above is placed into the bottom of the infusion machine, and the infusion machine is actuated for approximately two to five hours. During this actuation, the dried and coated potato is infused into the mixture to form an infused mixture, with an increase in time resulting in increased potency of the infused product. The infusion machine is turned off, and the infused mixture is dripped into a jar or container.

Next, the beeswax is introduced to a container, such as a glass measuring cup, which is placed into a pot of boiling water for a sufficient period to melt the beeswax (i.e., to raise the temperature of the beeswax above its melting temperature of approximately 145 degrees Fahrenheit or 63 degrees Celsius). The melted beeswax is then poured into a canning jar, and the infused mixture is added to the melted beeswax. The resultant mixture is allowed to cool, and the beeswax hardens. The combination of the infused mixture and the hardened beeswax forms an ointment that is suitable for application topically on the skin of a human to assist in clearing skin from skin blemishes such as acne.

To form a balm in accordance with this Example, the same procedure, but the relative amount of beeswax is increased to 1.25 to 1.5 fluid ounces while the remainder of the components relative amounts remains the same.

In still yet another example, an ointment used on dark spots for brightening the skin is formed from the ingredients/components described in Table 3 below according to the following procedure:

TABLE 3

| Ingredient/Component | Weight or Volume |
|---|---|
| Organic Jojoba Oil | 10.25 fluid ounces |
| Organic Rosehip Oil | 0.5 fluid ounces |
| Organic Lemon Oil | 0.25 fluid ounces |
| Organic Black Seed Oil | 0.25 fluid ounces |
| Organic Frankincense Oil | 0.5 fluid ounces |
| Organic Vitamin E Oil | 0.25 fluid ounces |
| Organic Neroli Oil | 0.25 fluid ounces |
| Organic Neem Oil | 0.25 fluid ounces |
| Large Organic Potato | ½, shredded (about 140 grams) |
| Organic Baking Soda | ½ cup (standard measuring cup) |
| Organic Apple Cider Vinegar | ½ cup (standard measuring cup - about 4 fluid ounces) |
| Pure Beeswax | 1.25 fluid ounces (ointment) or 1.5 fluid ounces (balm) |

First, the ½ of a large size potato is shredded and placed on a dish. The shredded potato is soaked in a mixture of the organic baking soda and organic apple cider vinegar for 20 minutes. The shredded potato coated with the organic baking soda and organic apple cider vinegar is allowed to dry at room temperature to form a dried and coated potato. The dried and coated potato may be moist to the touch.

The dried and coated potato is introduced to an infusion machine, here a LEVO brand infuser such as the LEVO 2 or LEVO Lux infuser. The mixture of the oils, totaling 12.5 fluid ounces as listed above is placed into the bottom of the infusion machine, and the infusion machine is actuated for approximately two to five hours. During this actuation, the dried and coated potato is infused into the mixture to form an infused mixture, with an increase in time resulting in increased potency of the infused product. The infusion machine is turned off, and the infused mixture is dripped into a jar or container.

Next, the beeswax is introduced to a container, such as a glass measuring cup, which is placed into a pot of boiling water for a sufficient period to melt the beeswax (i.e., to raise the temperature of the beeswax above its melting temperature of approximately 145 degrees Fahrenheit or 63 degrees Celsius). The melted beeswax is then poured into a canning jar, and the infused mixture is added to the melted beeswax. The resultant mixture is allowed to cool, and the beeswax hardens. The combination of the infused mixture and the hardened beeswax forms an ointment that is suitable for application topically on the skin of a human to treat dark spots or brighten the skin.

To form a balm in accordance with this Example, the same procedure, but the relative amount of beeswax is increased to 1.25 to 1.5 fluid ounces while the remainder of the components relative amounts remains the same.

In still yet another example, an ointment used for providing a "youthful radiance" to the skin is formed from the ingredients/components described in Table 4 below according to the following procedure:

TABLE 4

| Ingredient/Component | Weight or Volume |
|---|---|
| Organic Jojoba Oil | 10.25 fluid ounces |
| Organic Rosehip Oil | 0.5 fluid ounces |
| Organic Lavender Oil | 0.25 fluid ounces |
| Organic Frankincense Oil | 0.25 fluid ounces |
| Organic Vitamin E Oil | 0.25 fluid ounces |
| Organic Rosemary Oil | 0.25 fluid ounces |
| Organic Neroli Oil | 0.25 fluid ounces |
| Organic Black Seed Oil | 0.25 fluid ounces |
| Large Organic Potato | ½, shredded (about 140 grams) |
| Organic Baking Soda | ½ cup (standard measuring cup) |

TABLE 4-continued

| Ingredient/Component | Weight or Volume |
|---|---|
| Organic Apple Cider Vinegar | ½ cup (standard measuring cup - about 4 fluid ounces) |
| Pure Beeswax | 1.25 fluid ounces (ointment) or 1.5 fluid ounces (balm) |

First, the ½ of a large size potato is shredded and placed on a dish. The shredded potato is soaked in a mixture of the organic baking soda and organic apple cider vinegar for 20 minutes.

The shredded potato coated with the organic baking soda and organic apple cider vinegar is allowed to dry at room temperature to form a dried and coated potato. The dried and coated potato may be moist to the touch.

The dried and coated potato is introduced to an infusion machine, here a LEVO brand infuser such as the LEVO 2 or LEVO Lux infuser. The mixture of the oils, totaling 12.5 fluid ounces as listed above is placed into the bottom of the infusion machine, and the infusion machine is actuated for approximately two to five hours. During this actuation, the dried and coated potato is infused into the mixture to form an infused mixture, with an increase in time resulting in increased potency of the infused product. The infusion machine is turned off, and the infused mixture is dripped into a jar or container.

Next, the beeswax is introduced to a container, such as a glass measuring cup, which is placed into a pot of boiling water for a sufficient period to melt the beeswax (i.e., to raise the temperature of the beeswax above its melting temperature of approximately 145 degrees Fahrenheit or 63 degrees Celsius). The melted beeswax is then poured into a canning jar, and the infused mixture is added to the melted beeswax. The resultant mixture is allowed to cool, and the beeswax hardens. The combination of the infused mixture and the hardened beeswax forms an ointment that is suitable for application topically on the skin of a human provide "youthful radiance" to the skin.

To form a balm in accordance with this Example, the same procedure, but the relative amount of beeswax is increased to 1.25 to 1.5 fluid ounces while the remainder of the components relative amounts remains the same.

In still yet a further example, an ointment used for use on stretchmarks on the skin is formed from the ingredients/components described in Table 5 below according to the following procedure:

TABLE 5

| Ingredient/Component | Weight or Volume |
|---|---|
| Organic Jojoba Oil | 10.25 fluid ounces |
| Organic Frankincense Oil | 0.25 fluid ounces |
| Organic Rosehip Oil | 0.25 fluid ounces |
| Organic Neroli Oil | 0.25 fluid ounces |
| Organic Neem Oil | 0.25 fluid ounces |
| Organic Lavender Oil | 0.25 fluid ounces |
| Organic Vitamin E Oil | 0.25 fluid ounces |
| Organic Ginger Oil | 0.25 fluid ounces |
| Pure Aloe Vera | 0.25 fluid ounces |
| Large Organic Potato | ½, shredded (about 140 grams) |
| Organic Baking Soda | ½ cup (standard measuring cup) |

TABLE 5-continued

| Ingredient/Component | Weight or Volume |
|---|---|
| Organic Apple Cider Vinegar | ½ cup (standard measuring cup - about 4 fluid ounces) |
| Pure Beeswax | 1.25 fluid ounces (ointment) or 1.5 fluid ounces (balm) |

First, the ½ of a large size potato is shredded and placed on a dish. The shredded potato is soaked in a mixture of the organic baking soda and organic apple cider vinegar for 20 minutes. The shredded potato coated with the organic baking soda and organic apple cider vinegar is allowed to dry at room temperature to form a dried and coated potato. The dried and coated potato may be moist to the touch.

The dried and coated potato is introduced to an infusion machine, here a LEVO brand infuser such as the LEVO 2 or LEVO Lux infuser. The mixture of the oils, totaling 12.5 fluid ounces as listed above is placed into the bottom of the infusion machine, and the infusion machine is actuated for approximately two to five hours. During this actuation, the dried and coated potato is infused into the mixture to form an infused mixture, with an increase in time resulting in increased potency of the infused product. The infusion machine is turned off, and the infused mixture is dripped into a jar or container.

Next, the beeswax is introduced to a container, such as a glass measuring cup, which is placed into a pot of boiling water for a sufficient period to melt the beeswax (i.e., to raise the temperature of the beeswax above its melting temperature of approximately 145 degrees Fahrenheit or 63 degrees Celsius). The melted beeswax is then poured into a canning jar, and the infused mixture is added to the melted beeswax. The resultant mixture is allowed to cool, and the beeswax hardens. The combination of the infused mixture and the hardened beeswax forms an ointment that is suitable for application topically on the skin of a human provide "youthful radiance" to the skin.

To form a balm in accordance with this Example, the same procedure, but the relative amount of beeswax is increased to 1.25 to 1.5 fluid ounces while the remainder of the components relative amounts remains the same.

The disclosure has been described in an illustrative manner, and it is to be understood that the terminology which has been used is intended to be in the nature of words of description rather than of limitation. As is now apparent to those skilled in the art, many modifications and variations of the subject disclosure are possible in light of the above teachings. It is, therefore, to be understood that within the scope of the appended claims, wherein reference numerals are merely for convenience and are not to be in any way limiting, the disclosure may be practiced otherwise than as specifically described.

What is claimed is:

1. An ointment or balm suitable for topical application on a human or ingestion by the human, said ointment or balm formed according to the following method:

forming a soaked potato by soaking a shredded potato in a mixture of baking soda and vinegar with the vinegar suitable for culinary use;

forming a dried and coated potato by drying the soaked potato to remove residual moisture;

introducing the dried and coated potato to an infusing machine;

placing an oil mixture into the infusing machine;

forming an infused product by actuating the infusing machine to infuse the dried and coated potato with the oil mixture;

melting a quantity of beeswax;

combining the infused product with the quantity of melted beeswax; and cooling the beeswax below its melting temperature to form the ointment or the balm, wherein the shredded potato remains in the formed ointment or balm, wherein a volume of beeswax relative to a volume of the oil mixture varies from 0.5 to 2 fluid ounces of beeswax relative to 12 to 13 fluid ounces of the oil mixture in the ointment or balm, and wherein a weight of the shredded potato relative to the volume of the oil mixture varies from 140 to 170 grams of potato relative to 10 to 15 liquid ounces of the oil mixture.

2. An ointment suitable for topical application on a human or ingestion by the human, said ointment comprising:

an infused product comprising:

a shredded potato, a mixture of vinegar and baking soda coated onto said shredded potato to form a dried and coated shredded potato with the vinegar suitable for culinary use, an oil mixture infused into said dried and coated shredded potato; and beeswax combined with said infused product, wherein the shredded potato remains in the ointment, wherein a volume of beeswax relative to a volume of said oil mixture in the ointment varies from 1.0 to 1.25 fluid ounces of beeswax relative to 12 to 13 fluid ounces of said oil mixture, and wherein a weight of the shredded potato relative to the volume of the oil mixture varies from 140 to 170 grams of potato relative to 10 to 15 liquid ounces of the oil mixture.

3. A balm suitable for topical application on a human or ingestion by the human, said balm comprising:

an infused product comprising:

a shredded potato, a mixture of vinegar and baking soda coated onto said shredded potato to form a dried and coated shredded potato with the vinegar suitable for culinary use, an oil mixture infused into said dried and coated shredded potato; and beeswax combined with said infused product, wherein the shredded potato remains in the balm, wherein a volume of beeswax relative to a volume of said oil mixture in the balm varies from 1.25 to 1.50 fluid ounces of beeswax relative to 12 to 13 fluid ounces of said oil mixture, and wherein a weight of the shredded potato relative to the volume of the oil mixture varies from 140 to 170 grams of potato relative to 10 to 15 liquid ounces of the oil mixture.

4. The ointment of claim 2, wherein said mixture of vinegar and water comprises a mixture of organic apple cider vinegar and water.

5. The ointment of claim 2, wherein a weight ratio of baking soda to vinegar in said mixture of baking soda and vinegar is 50:50.

6. The ointment of claim 2, wherein the oil mixture includes a carrier oil and one or more essential oils.

7. The ointment of claim 6, wherein the carrier oil is jojoba oil or almond oil, and wherein the one or more essential oils is selected from the group consisting of lavender oil, tea tree oil, frankincense oil, peppermint oil, lemon oil, lemongrass oil, orange oil, rosemary oil, and bergamot oil.

8. The ointment of claim 6, wherein the one or more essential oils is selected from the group consisting of lavender oil, tea tree oil, frankincense oil, peppermint oil, lemon oil, lemongrass oil, orange oil, rosemary oil, and bergamot oil.

9. The ointment of claim 2, wherein the mixture further comprises aloe vera.

10. The balm of claim 3, wherein said mixture of vinegar and water comprises a mixture of organic apple cider vinegar and water.

11. The balm of claim 3, wherein a weight ratio of baking soda to vinegar in said mixture of baking soda and vinegar is 50:50.

12. The balm of claim 3, wherein the oil mixture includes a carrier oil and one or more essential oils.

13. The balm of claim 12, wherein the carrier oil is jojoba oil or almond oil, and wherein the one or more essential oils is selected from the group consisting of lavender oil, tea tree oil, frankincense oil, peppermint oil, lemon oil, lemongrass oil, orange oil, rosemary oil, and bergamot oil.

14. The balm of claim 12, wherein the one or more essential oils is selected from the group consisting of lavender oil, tea tree oil, frankincense oil, peppermint oil, lemon oil, lemongrass oil, orange oil, rosemary oil, and bergamot oil.

15. The balm of claim 3, wherein the mixture further comprises aloe vera.

16. The ointment or balm of claim 1, wherein the volume of beeswax relative to the volume of the oil mixture in the ointment varies from 1 to 1.25 fluid ounces of beeswax relative to 12 to 13 fluid ounces of the oil mixture.

17. The ointment or balm of claim 1, wherein the volume of beeswax relative to the volume of the oil mixture in the balm varies from 1.25 to 1.5 fluid ounces of beeswax relative to 12 to 13 fluid ounces of the oil mixture.

18. A method for forming an ointment or a balm suitable for topical application on a human or ingestion by the human, said method comprising:

forming a soaked potato by soaking a shredded potato in a mixture of baking soda and vinegar with the vinegar suitable for culinary use;

forming a dried and coated potato by drying the soaked potato to remove residual moisture;

introducing the dried and coated potato to an infusing machine;

placing an oil mixture into the infusing machine;

forming an infused product by actuating the infusing machine to infuse the dried and coated potato with the oil mixture;

melting a quantity of beeswax;

combining the infused product with the quantity of melted beeswax; and cooling the beeswax below its melting temperature to form the ointment or the balm, wherein the shredded potato remains in the formed ointment or balm, wherein a volume of beeswax relative to a volume of the oil mixture varies from 0.5 to 2 fluid ounces of beeswax relative to 12 to 13 fluid ounces of the oil mixture in the ointment or balm, and wherein a weight of the shredded potato relative to the volume of the oil mixture varies from 140 to 170 grams of potato relative to 10 to 15 liquid ounces of the oil mixture.

* * * * *